US006380459B1

(12) United States Patent
Perera et al.

(10) Patent No.: US 6,380,459 B1
(45) Date of Patent: Apr. 30, 2002

(54) COMPOSITIONS AND METHODS FOR THE MODIFICATION OF GENE EXPRESSION

(75) Inventors: J. Ranjan Perera; Stephen J. Rice, both of Auckland (NZ)

(73) Assignees: Genesis Research & Development Corporation Ltd.; Fletcher Challenge Forests Ltd., both of (NZ)

( * ) Notice: Subject to any disclaimer, the term of this patent is extended or adjusted under 35 U.S.C. 154(b) by 0 days.

(21) Appl. No.: 09/276,599

(22) Filed: Mar. 25, 1999

(51) Int. Cl.[7] .................. C12N 15/09; C12N 15/29; C12N 15/82; A01H 5/00

(52) U.S. Cl. ............... 800/278; 800/278; 800/295; 800/298; 800/286; 435/69.1; 435/320.1; 435/419; 435/468; 536/23.1; 536/23.2; 536/23.6; 536/24.1; 536/24.5

(58) Field of Search .................. 800/278, 295, 800/298, 286; 435/69.1, 320.1, 419, 468; 536/23.1, 23.2, 23.6, 24.1, 24.5

(56) References Cited

U.S. PATENT DOCUMENTS

| 5,510,474 A | | 4/1996 | Quail et al. |
| 5,639,952 A | | 6/1997 | Quail et al. ............ 800/205 |
| 5,656,496 A | | 8/1997 | Quail et al. ............ 435/320 |
| 5,750,385 A | | 5/1998 | Shewmaker et al. |
| 5,910,415 A | * | 6/1999 | Hodges et al. ............ 435/6 |

FOREIGN PATENT DOCUMENTS

WO          9747756        12/1997 ........... C12N/15/82

OTHER PUBLICATIONS

Kojima et al, "Structure of the pine (*Pinus thunbergii*) chloropyll a/b–binding protein gene expressed in the absence of light", 1992, Plant Molecular Biology, vol. 19 pp. 405–410.*

Kim et al, "A 20 nucleotide upstream element is essential for the nopaline synthase (nos) prometer activity", 1994, Plant Molecular Biology vol. 24 pp. 105–117.*

Kojima et al, Genbank Accession No. X61915 S39573, 1991.*

GenPept Assession No. CAA63531; submitted Nov. 9, 1995 by Ruiter, R.K.

GenPept Assession No. CAA10056; submitted Nov. 12, 1998 by Fruehling, M.

GenBank Assession No. M55147 X51434; Liaud, M. and Cerff, R., *Proc. Nat'l Acad. Sci.*, vol. 87, No. 22, pp. 8918–8922 (1990).

GenBank Assession No. X74814; submitted Aug. 27, 1993 by Poeyudomenge, O., et al.

GenBank Assession No. AF077743; submitted Jul. 13, 1998 by Rehli, M., et al.

GenBank Assession No. U73588; submitted Oct. 7, 1996 by Pere–Grau, L., et al.

GenBank Assession No. U90350; submitted Feb. 24, 1997 by Walden, A.R., et al.

GenBank Assession No. AF041463; submitted Jan. 6, 1998 by Suhandono, et al.

Callis, Judy et al., "Ubiquitin Extension Proteins of *Arabidopsis thaliana*", *JBC*, vol. 265, pp. 12486–12493 (1990).

Belknap, William R. and Garbarino, Joan E. "The Role of ubiquitin in plant senescence and stress responses," *Trends in Plant Science* vol. 1, No. 10:331–335, Oct. 1996.

Scharf, Klaus–Dieter, Materna, Tilo, Trueter, Eckardt, and Nover, Lutz. "Heat Stress Promoters and Transcription Factors," *Results Probl Cell Differ* 20:125–62, 1994.

* cited by examiner

*Primary Examiner*—Phuong T. Bui
*Assistant Examiner*—Medina A. Ibrahim
(74) *Attorney, Agent, or Firm*—Janet Sleath; Ann W. Speckman

(57) ABSTRACT

Novel isolated plant polynucleotide promoter sequences are provided, together with DNA constructs comprising such polynucleotides. Methods for using such constructs in modulating the transcription of DNA sequences of interest are also disclosed, together with transgenic plants comprising such constructs.

17 Claims, No Drawings

COMPOSITIONS AND METHODS FOR THE MODIFICATION OF GENE EXPRESSION

TECHNICAL FIELD OF THE INVENTION

This invention relates to the regulation of gene transcription and/or expression. More specifically, this invention relates to polynucleotide regulatory sequences isolated from plants that are capable of initiating and driving the transcription of genes, and the use of such regulatory sequences in the modification of transcription of endogenous and/or heterologous genes.

BACKGROUND OF THE INVENTION

Gene expression is regulated, in part, by the cellular processes involved in transcription. During transcription, a single-stranded RNA complementary to the DNA sequence to be transcribed is formed by the action of RNA polymerases. Initiation of transcription in eucaryotic cells is regulated by complex interactions between cis-acting DNA motifs, located within the gene to be transcribed, and trans-acting protein factors. Among the cis-acting regulatory regions are sequences of DNA, termed promoters to which RNA polymerase is first bound, either directly or indirectly As used herein, the term "promoter" refers to the 5' untranslated region of a gene that is associated with transcription and which generally includes a transcription start site. Other cis-acting DNA motifs, such as enhancers, may be situated further up- and/or down-stream from the initiation site.

Both promoters and enhancers are generally composed of several discrete, often redundant, elements each of which may be recognized by one or more trans-acting regulatory proteins, known as transcription factors. Promoters generally comprise both proximal and more distant elements. For example, the so-called TATA box, which is important for the binding of regulatory proteins, is generally found about 25 basepairs upstream from the initiation site. The so-called CAAT box is generally found about 75 basepairs upstream of the initiation site. Promoters generally contain between about 100 and 1000 nucleotides, although longer promoter sequences are possible.

For the development of transgenic plants, constitutive promoters that drive strong transgene expression are preferred. Currently, the only available constitutive plant promoter that is widely used is derived from Cauliflower Mosaic Virus. Furthermore, there exists a need for plant-derived promoters for use in transgenic food plants due to public conceptions regarding the use of viral promoters. Few gymnosperm promoters have been cloned and those derived from angiosperms have been found to function poorly in gymnosperms. There thus remains a need in the art for polynucleotide promoter regions isolated from plants for use in modulating transcription and expression of genes in transgenic plants.

SUMMARY OF THE INVENTION

Briefly, isolated polynucleotide regulatory sequences from eucalyptus and pine that are involved in the regulation of gene expression are disclosed, together with methods for the use of such polynucleotide regulatory regions in the modification of expression of endogenous and/or heterologous genes in transgenic plants. In particular, the present invention provides polynucleotide promoter sequences from 5' untranslated regions of plant genes that initiate and regulate transcription of DNA sequences placed under their control.

In a first aspect, isolated polynucleotide promoter sequences are provided that comprise a DNA sequence selected from the group consisting of: (a) sequences recited in SEQ ID NO: 2–14 and 20; (b) complements of the sequences recited in SEQ ID NO: 2–14 and 20; (c) reverse complements of the sequences recited in SEQ ID NO: 2–14,20; (d) reverse sequences of the sequences recited in SEQ ID NO: 2–14 and 20; and (e) sequences having either 40%, 60%, 75% or 90% identical nucleotides, as defined herein, to a sequence of (a)–(d).

In a related aspect, the present invention provides DNA constructs comprising, in the 5'–3' direction, a polynucleotide promoter sequence of the present invention, a DNA sequence to be transcribed, and a gene termination sequence. The DNA sequence to be transcribed may comprise an open reading frame of a DNA sequence that encodes a polypeptide of interest or may be a non-coding, or untranslated, region of a DNA sequence of interest. The open reading frame may be orientated in either a sense or antisense direction. Preferably, the gene termination sequence is functional in a host plant. Most preferably, the gene termination sequence is that of the gene of interest, but others generally used in the art, such as the *Agrobacterium tumefaciens* nopalin synthase terminator may be usefully employed in the present invention. The DNA construct may further include a marker for the identification of transformed cells.

In a further aspect, transgenic plant cells comprising the DNA constructs of the present invention are provided, together with organisms, such as plants, comprising such transgenic cells, and fruits and seeds of such plants.

In yet another aspect, methods for modifying gene expression in a target organism, such as a plant, are provided, such methods including stably incorporating into the genome of the organism a DNA construct of the present invention. In a preferred embodiment, the target organism is a plant, more preferably a woody plant, most preferably selected from the group consisting of eucalyptus and pine species, most preferably from the group consisting of *Eucalyptus grandis* and *Pinus radiata*.

In another aspect, methods for producing a target organism, such as a plant, having modified gene expression are provided, such methods comprising transforming a plant cell with a DNA construct of the present invention to provide a transgenic cell, and cultivating the transgenic cell under conditions conducive to regeneration and mature plant growth.

In other aspects, methods for identifying a gene responsible for a desired function or phenotype are provided, the methods comprising transforming a plant cell with a DNA construct comprising a polynucleotide promoter sequence of the present invention operably linked to a gene to be tested, cultivating the plant cell under conditions conducive to regeneration and mature plant growth to provide transgenic a plant; and comparing the phenotype of the transgenic plant with the phenotype of non-transformed, or wild-type, plants.

In yet a further aspect, the present invention provides an isolated polynucleotide from *Pinus radiata* that encodes ubiquitin. In specific embodiments, the isolated polynucleotide comprises a DNA sequence selected from the group consisting of: (a) a sequence recited in SEQ ID NO: 1; (b) complements of the sequence recited in SEQ ID NO: 1; (c) reverse complements of the sequence recited in SEQ ID NO: 1; (d) reverse sequences of the sequence recited in SEQ ID NO: 1; and (e) sequences having either 40%, 60%, 75% or 90% identical nucleotides, as defined herein, to a sequence of (a)–(d). Polypeptides encoded by such polynucleotides are also provided, together with DNA constructs comprising such polynucleotides, and host cells and transgenic organisms, for example plants, transformed with such DNA constructs.

In yet further aspects, the present invention provides isolated polynucleotides comprising the DNA sequence of SEQ ID NO: 21, or a complement, reverse complement or variant of SEQ ID NO: 21, together with DNA constructs comprising such polynucleotides and cells transformed with such sequences. As discussed below, removal of the sequence of SEQ ID NO: 21 from a polynucleotide that comprises the sequence of SEQ ID NO: 21 may enhance expression of the polynucleotide. Conversely, the inclusion of the sequence of SEQ ID NO: 21 in a DNA construct comprising a polynucleotide of interest may decrease expression of the polynucleotide.

The above-mentioned and additional features of the present invention and the manner of obtaining them will become apparent, and the invention will be best understood by reference to the following more detailed description. All references disclosed herein are hereby incorporated by reference in their entirety as if each was incorporated individually.

DETAILED DESCRIPTION OF THE INVENTION

The present invention provides isolated polynucleotide regulatory regions that may be employed in the manipulation of plant phenotypes. More specifically, polynucleotide promoter sequences isolated from pine and eucalyptus are disclosed. As discussed above, promoters are components of the cellular "transcription apparatus" and are involved in the regulation of gene expression. Both tissue- and temporal-specific gene expression patterns have been shown to be initiated and controlled by promoters during the natural development of a plant. The isolated polynucleotide promoter sequences of the present invention may thus be employed in the modification of growth and development of plants, and of cellular responses to external stimuli, such as environmental factors and disease pathogens.

Using the methods and materials of the present invention, the amount of a specific polypeptide of interest may be increased or reduced by incorporating additional copies of genes encoding the polypeptide, operably linked to an inventive promoter sequence, into the genome of a target organism, such as a plant. Similarly, an increase or decrease in the amount of the polypeptide may be obtained by transforming the target plant with antisense copies of such genes.

In one embodiment, the present invention provides a polynucleotide sequence isolated from *Pinus radiata* that encodes a ubiquitin polypeptide. The full-length sequence of this polynucleotide is provided in SEQ ID NO: 1, with the sequence of the promoter region including an intron being provided in SEQ ID NO: 2 and the sequence of the promoter region excluding the intron being provided in SEQ ID NO: 3. In a related embodiment, the present invention provides isolated polypeptides encoded by the isolated polynucleotide of SEQ ID NO: 1.

In further embodiments, the following isolated polynucleotide promoter sequences from *Pinus radiata* are provided: a cell division control (CDC) gene promoter (SEQ ID NO: 4); a xylogenesis-specific promoter (SEQ ID NO: 5); a 4-coumarate Co-A ligase (4CL) promoter (SEQ ID NO: 6); and a root-specific promoter (SEQ ID NO: 13 and 14). The following isolated polynucleotide promoter sequences from *Eucalyptus grandis* are also provided: a cellulose synthase promoter (SEQ ID NO: 7–8 and 20); a leaf-specific promoter (SEQ ID NO: 9–11); and an O-methyl transferase (OMT) promoter (SEQ ID NO: 12). Complements of the inventive isolated polynucleotides, reverse complements of such isolated polynucleotides and reverse sequences of such isolated polynucleotides are also provided, together with variants of such sequences. The present invention also encompasses polynucleotide sequences that differ from the disclosed sequences but which, due to the degeneracy of the genetic code, encode a polypeptide which is the same as that encoded by a polynucleotide sequence disclosed herein.

The term "polynucleotide(s)," as used herein, means a single or double-stranded polymer of deoxyribonucleotides or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. (1995), Antisense techniques, *Methods in Enzymol.* 254(23): 363–375 and Kawasaki et al. (1996), *Artific. Organs* 20 (8): 836–848.

The term "polypeptide", as used herein, encompasses amino acid chains of any length including full length proteins, wherein amino acid residues are linked by covalent peptide bonds. Polypeptides of the present invention may be naturally purified products, or may be produced partially or wholly using recombinant techniques. The term "polypeptide encoded by a polynucleotide" as used herein, includes polypeptides encoded by a nucleotide sequence which includes the partial isolated DNA sequences of the present invention.

All of the polynucleotides and polypeptides described herein are isolated and purified, as those terms are commonly used in the art.

The definition of the terms "complement", "reverse complement" and "reverse sequence", as used herein, is best illustrated by the following example. For the sequence 5' AGGACC 3', the complement, reverse complement and reverse sequence are as follows:

```
complement              3' TCCTGG 5'
reverse complement      3' GGTCCT 5'
reverse sequence        5' CCAGGA 3'.
```

As used herein, the term "variant" covers any sequence which has at least about 40%, more preferably at least about 60%, more preferably yet at least about 75% and most preferably at least about 90% identical residues (either nucleotides or amino acids) to a sequence of the present invention. The percentage of identical residues is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical nucleotides in a specified region may be determined against another polynucleotide, using computer algorithms that are publicly available. Two exemplary algorithms for aligning and identifying the similarity of polynucleotide sequences are the BLASTN and EASTA algorithms. The similarity of polypeptide sequences may be examined using the BLASTP algorithm. Both the BLASTN and BLASTP software are available on the NCBI anonymous FTP server. The BLASTN algorithm version 2.0.4 [Feb. 24, 1998], set to the default parameters described in the documentation and distributed with the algorithm, is preferred for use in the determination of variants according to the present invention. The use of the BLAST family of algorithms, including BLASTN and BLASTP, is described at NCBI's website and in the publication of Altschul, Stephen F., et al. (1997), "Gapped BLAST and PSI-BLAST: a new generation of protein database search programs", *Nucleic Acids Res.* 25:3389–3402. The computer algorithm FASTA is available on the Internet and, Version 2.u4, February 1996, set to the default parameters described in the documentation and distributed with the algorithm, is preferred for use in the determination of variants according to the present invention. The use of the FASTA algorithm is described in W. R. Pearson and D. J. Lipman, "Improved Tools for Biological Sequence Analysis," *Proc. Natl. Acad. Sci. USA* 85:2444–2448 (1988) and W. R. Pearson, "Rapid and Sensitive Sequence Comparison with FASTP and FASTA," *Methods in Enzymology* 183:63–98 (1990).

The following running parameters are preferred for determination of alignments and similarities using BLASTN that contribute to the E values and percentage identity: Unix running command: blastall -p blastn -d embldb -e 10 -G 1 -E 1 -r 2 -v 50 -b 50 -i queryseq -o results; and parameter default values:

-p Program Name [String]
-d Database [String]
-e Expectation value (E) [Real]
-G Cost to open a gap (zero invokes default behavior) [Integer]
-E Cost to extend a gap (zero invokes default behavior) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional For BLASTP the following running parameters are preferred: blastall -p blastp -d swissprotdb -e 10 -G 1 -E 1 -v 50 -b 50 -i queryseq -o results -p Program Name [String]
-d Database [String]
-e Expectation value (E) [Real]
-G Cost to open a gap (zero invokes default behavior) [Integer]
-E Cost to extend a gap (zero invokes default behavior) [Integer]
-v Number of one-line descriptions (v) [Integer]
-b Number of alignments to show (b) [Integer]
-I Query File [File In]
-o BLAST report Output File [File Out] Optional The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Variant polynucleotide sequences will generally hybridize to the recited polynucleotide sequence under stringent conditions. As used herein, "stringent conditions" refers to prewashing in a solution of 6X SSC, 0.2% SDS; hybridizing at 65° C., 6X SSC, 0.2% SDS overnight; followed by two washes of 30 minutes each in 1X SSC, 0.1% SDS at 65° C. and two washes of 30 minutes each in 0.2X SSC, 0.1% SDS at 65° C.

As used herein, the term "x-mer," with reference to a specific value of "x," refers to a polynucleotide comprising at least a specified number ("x") of contiguous residues of any of the polynucleotides identified as SEQ ID NO: 1–14 and 20. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1–14 and 20 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 1–14 and 20 or a variant of one of the polynucleotides identified as SEQ ID NO: 1–14 and 20.

The inventive polynucleotides may be isolated by high throughput sequencing of cDNA libraries prepared from *Eucalyptus grandis* and *Pinus radiata* as described below. Alternatively, oligonucleotide probes based on the sequences provided in SEQ ID NO: 1–14 and 20 can be synthesized and used to identify positive clones in either cDNA or genomic DNA libraries from *Eucalyptus grandis* and *Pinus radiata* by means of hybridization or PCR techniques. Probes can be shorter than the sequences provided herein but should be at least about 10, preferably at least about 15 and most preferably at least about 20 nucleotides in length. Hybridization and PCR techniques suitable for use with such oligonucleotide probes are well known in the art, and include those taught by Sambrook et al., (*Molecular Cloning: A Laboratory Manual,* Cold Spring Harbor Laboratories, Cold Spring Harbor, N.Y., 1989). Positive clones may be analyzed by restriction enzyme digestion, DNA sequencing and the like.

In addition, the DNA sequences of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

Polypeptides of the present invention may be prepared recombinantly by inserting a DNA sequence that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a DNA molecule that encodes recombinant polypeptide. Suitable host cells include prokaryotes, yeast and higher eukaryotic cells.

As noted above, the inventive polynucleotide promoter sequences may be employed in DNA constructs to drive transcription and/or expression of a DNA sequence of interest. The DNA sequence of interest may be either endogenous or heterologous to the organism, for example plant, to be transformed. The inventive DNA constructs may thus be employed to modulate levels of transcription and/or expression of a DNA sequence, for example gene, that is present in the wild-type plant, or may be employed to provide transcription and/or expression of a DNA sequence that is not found in the wild-type plant.

In certain embodiments, the DNA sequence of interest comprises an open reading frame that encodes a target polypeptide. The open reading frame is inserted in the DNA construct in either a sense or antisense orientation, such that transformation of a target plant with the DNA construct will lead to a change in the amount of polypeptide compared to the wild-type plant. Transformation with a DNA construct comprising an open reading frame in a sense orientation will generally result in over-expression of the selected polypeptide, while transformation with a DNA construct comprising an open reading frame in an antisense orientation will generally result in reduced expression of the selected polypeptide. A population of plants transformed with a DNA construct comprising an open reading frame in either a sense or antisense orientation may be screened for increased or reduced expression of the polypeptide in question using techniques well known to those of skill in the art, and plants having the desired phenotypes may thus be isolated.

Alternatively, expression of a target polypeptide may be inhibited by inserting a portion of the open reading frame, in either sense or antisense orientation, in the DNA construct. Such portions need not be full-length but preferably comprise at least 25 and more preferably at least 50 residues of the open reading frame. A much longer portion or even the full length DNA corresponding to the complete open reading frame may be employed. The portion of the open reading frame does not need to be precisely the same as the endogenous sequence, provided that there is sufficient sequence similarity to achieve inhibition of the target gene. Thus a sequence derived from one species may be used to inhibit expression of a gene in a different species.

In further embodiments, the inventive DNA constructs comprise a DNA sequence including an untranslated, or non-coding, region of a gene coding for a target polypeptide, or a DNA sequence complementary to such an untranslated region. Examples of untranslated regions which may be usefully employed in such constructs include introns and 5'-untranslated leader sequences. Transformation of a target plant with such a DNA construct may lead to a reduction in the amount of the polypeptide expressed in the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

Alternatively, regulation of polypeptide expression can be achieved by inserting appropriate sequences or subsequences (e.g. DNA or RNA) in ribozyme constructs (McIntyre C L, Manners J M, *Transgenic Res.,* 5(4): 257–262, 1996). Ribozymes are synthetic RNA molecules that comprise a hybridizing region complementary to two regions, each of which comprises at least 5 contiguous nucleotides in a mRNA molecule encoded by one of the inventive polynucleotides. Ribozymes possess highly specific endonuclease activity, which autocatalytically cleaves the mRNA.

The DNA sequence of interest is operably linked to a polynucleotide promoter sequence of the present invention such that a host cell is able to transcribe an RNA from the promoter sequence linked to the DNA sequence of interest. The gene promoter sequence is generally positioned at the 5' end of the DNA sequence to be transcribed. Use of a constitutive promoter, such as the ubiquitin polynucleotide promoter sequence of SEQ ID NO: 2 and 3, will affect transcription of the DNA sequence of interest in all parts of the transformed plant. Use of a tissue specific promoter, such as the leaf-specific promoter of SEQ ID NO: 9–11 or the root-specific promoter of SEQ ID NO: 13 and 14, will result in production of the desired sense or antisense RNA only in the tissue of interest. Temporally regulated promoters, such as the xylogenesis-specific promoter of SEQ ID NO: 5, can be employed to effect modulation of the rate of DNA transcription at a specific time, during development of a transformed plant. With DNA constructs employing inducible gene promoter sequences, the rate of DNA transcription can be modulated by external stimuli, such as light, heat, anaerobic stress, alteration in nutrient conditions and the like.

The inventive DNA constructs further comprise a gene termination sequence which is located 3' to the DNA sequence of interest. A variety of gene termination sequences which may be usefully employed in the DNA constructs of the present invention are well known in the art. One example of such a gene termination sequence is the 3' end of the *Agrobacterium tumefaciens* nopaline synthase gene. The gene termination sequence may be endogenous to the target plant or may be exogenous, provided the promoter is functional in the target plant. For example, the termination sequence may be from other plant species, plant viruses, bacterial plasmids and the like.

The DNA constructs of the present invention may also contain a selection marker that is effective in cells of the target organism, such as a plant, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al. in *Methods for Plant Molecular Biology*, A. Weissbach and H. Weissbach, eds., Academic Press Inc., San Diego, Calif. (1988)). Transformed cells can thus be identified by their ability to grow in media containing the antibiotic in question. Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Sambrook et al., (*Molecular Cloning: A Laboratory Manual*, Cold Spring Harbor Laboratories, Cold Spring Harbor, N.Y., 1989). The DNA construct of the present invention may be linked to a vector having at least one replication system, for example *E. coli*, whereby after each manipulation, the resulting construct can be cloned and sequenced and the correctness of the manipulation determined.

The DNA constructs of the present invention may be used to transform a variety of target organisms including, but not limited to, plants. Plants which may be transformed using the inventive constructs include both monocotyledonous angiosperms (e.g. grasses, corn, grains, oat, wheat and barley) and dicotyledonous angiosperms (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., *Biotechnology* 11:94–92, 1993), and larch (Huang et al., *In Vitro Cell* 27:201–207, 1991)). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. Other species which may be usefully transformed with the DNA constructs of the present invention include, but are not limited to: pines such as *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana;* other gymnosperms, such as *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata;* and Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus novaanglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni;* and hybrids of any of these species.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, dissociated cells, protoplasts, seeds, embryos, meristematic regions; cotyledons, hypocotyls, and the like. The preferred method for transforming eucalyptus and pine is a biolistic method using pollen (see, for example, Aronen 1996, Finish Forest Res. Papers vol. 595, 53pp) or easily regenerable embryonic tissues.

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: *In Vitro Embryogenesis of Plants.* Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement.* Redenbaugh, K., ed. CRC Press, Chapter 23, pp. 427–449, 1993). Transformed plants having the desired phenotype may be selected using techniques well known in the art. The resulting transformed plants may be reproduced sexually or asexually, using methods well known in the art, to give successive generations of transgenic plants.

As discussed above, the production of RNA in target cells can be controlled by choice of the promoter sequence, or by selecting the number of functional copies or the site of integration of the DNA sequences incorporated into the genome of the target host. A target organism may be transformed with more than one DNA construct of the present invention, thereby modulating the activity of more than gene. Similarly, a DNA construct may be assembled containing more than one open reading frame coding for a polypeptide of interest or more than one untranslated region of a gene coding for such a polypeptide.

The isolated polynucleotides of the present invention may also be employed as probes to isolate polynucleotide promoter sequences from other species, using techniques well known to those of skill in the art, such as routinely employed DNA hybridization and PCR techniques.

The following examples are offered by way of illustration and not by way of limitation.

EXAMPLE 1

Isolation and Characterization of a Ubiquitin Gene Promoter from *Pinus radiata*

*Pinus radiata* cDNA expression libraries were constructed and screened as follows. mRNA was extracted from plant tissue using the protocol of Chang et al. (*Plant Molecular Biology Reporter* 11:113–116 (1993)) with minor modifications. Specifically, samples were dissolved in CPC-RNAXB (100 mM Tris-Cl, pH 8,0; 25 mM EDTA; 2.0 M NaCl; 2%CTAB; 2% PVP and 0.05% Spermidine*3 HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems Division, Foster City, Calif.) according to the manufacturer's protocol.

DNA sequence for positive clones was obtained using a Perkin Elmer/Applied Biosystems Division Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

As described below, one of the most abundant sequences identified was an ubiquitin gene, hereinafter referred to as the "Super-Ubiquitin" gene.

Isolation of cDNA Clones Containing the Ubiquitin Gene

Sequences of cDNA clones with homology to the ubiquitin gene were obtained from high-throughput cDNA sequencing as described above. Sequences from several independent clones were assembled in a contig and a consensus sequence was generated from overlapping clones. The determined nucleotide sequence of the isolated Super Ubiquitin clone, comprising the promoter region (including an intron), coding region and 3' untranslated region (UTR) is provided in SEQ ID NO.1. The 5' UTR is represented by residues 1 to 2064, the intron by residues 1196 to 2033, and the coding region of the gene, which contains three direct repeats, by residues 2065 to 2751. The 3' UTR is 328 residues long (residues 2755 to 3083). The nucleotide sequence of the Super Ubiquitin promoter region only, including the intron, is given in SEQ ID NO.2. The nucleotide sequence of the Super Ubiquitin promoter region only, excluding the intron, is given in SEQ ID NO.3.

Ubiquitin proteins function as part of a protein degradation pathway, in which they covalently attach to proteins, thereby targeting them for degradation (for a review, see Belknap & Garbarino, Trends in Plant Sciences, volume 1, pp. 331–335, 1996). The protein is produced from a precursor polypeptide, encoded by a single mRNA. The Super Ubiquitin mRNA contains three copies of the ubiquitin monomer.

Cloning of the Super Ubiquitin Promoter

Fragments of the Super Ubiquitin promoter were cloned by two different PCR-based approaches.

Method 1: Long Distance Gene Walking PCR

Using "Long Distance Gene Walking" PCR (Min & Powell, *Biotechniques* 24:398–400, 1998), a 2 kb fragment was obtained that contained the entire coding region of the ubiquitin gene, a 900 bp intron in the 5' UTR and approximately 100 bp of the promoter.

To generate this fragment, 2 nested primers were designed from the 3' UTR of the Super Ubiquitin cDNA sequence isolated from pine. Generally, the 5' UTR is used for primer design to amplify upstream sequence. However, the available 5' UTR of Super Ubiquitin was very short, and two initial primers derived from this region failed to amplify any fragments. Therefore, the primers of SEQ ID NO: 15 and 16 were designed from the 3' UTR.

The method involved an initial, linear PCR step with pine genomic DNA as template using the primer of SEQ ID NO: 15, and subsequent C-tailing of the single stranded DNA product using terminal transferase. The second PCR-step used these fragments as template for amplification with the primer of SEQ ID NO: 16 and primer AP of SEQ ID NO: 17. The AP primer was designed to bind to the polyC tail generated by the terminal transferase. Both primers (SEQ ID NO: 16 and 17) contained a 5'-Not I restriction site for the cloning of products into the Not I site of a suitable vector. The final PCR product contained fragments of different sizes. These fragments were separated by electrophoresis and the largest were purified from the gel, digested with restriction endonuclease Not I and cloned in the Not I site of expression vector pBK-CMV (Stratagene, La Jolla, Calif.). The largest of these clones contained the complete coding region of the gene (no introns were found in the coding sequence) and a 5' UTR which contained a 900 bp intron.

Method 2: "Genome Walker" Kit

The Super Ubiquitin gene promoter was cloned using a "Genome Walker" kit (Clontech, Palo Alto, Calif.). This is also a PCR-based method, which requires 2 PCR primers to be constructed, one of which must be gene-specific. Although the ubiquitin coding region is highly conserved, the 5' UTR from different ubiquitin genes is not conserved and could therefore be used to design a gene-specific primer. A 2.2 kb fragment was amplified and subcloned in pGEM-T-easy (Promega, Madison, Wis.). Analysis by PCR and DNA sequencing showed that the clone contained 5' UTR sequence of the Super Ubiquitin gene, including the 900 bp intron and approximately 1 kb of putative promoter region. An intron in the 5' UTR is a common feature of plant polyubiquitin genes and may be involved in determining gene expression levels.

The gene specific primers used for these PCR reactions are provided in SEQ ID NO: 18 and 19.

Expression of Super Ubiquitin

Using primers derived from the gene-specific 5' and 3' UTR sequences, expression levels of Super Ubiquitin in different plant tissues was examined by means of RT-PCR. Super Ubiquitin was found to be expressed in all plant tissues examined, including branch phloem and xylem, feeder roots, fertilised cones, needles, one year old cones, pollen sacs, pollinated cones, root xylem, shoot buds, structural roots, trunk phloem and trunk. Expression of Super Ubiquitin in plant tissues was also demonstrated in a Northern blot assay using a PCR probe prepared from the 5'UTR.

Functional Analysis of the Super Ubiquitin Promoter

To test the function of the Super Ubiquitin promoter in plants, *Arabidopsis thaliana* were transformed with constructs containing the reporter gene for Green Fluorescent Protein (GFP) operably linked to either the Super Ubiquitin promoter of SEQ ID NO: 2 or SEQ ID NO: 3 (i.e., either with or without the intron). Constructs lacking a promoter were used as a negative control, with a plant T-DNA vector carrying a CaMV 35s promoter cloned in front of GFP being used as a positive control. The constructs were introduced into Arabidopsis via Agrobacterium-mediated transformation.

All the plant culture media were according to the protocol of Valvekens, D & Van Montagu (1988, *Proc. Natl. Acad. Sci USA* 85:5536–5540) with minor modifications. For root transformation, sterilized seeds were placed in a line on the surface of germination medium, the plates were placed on their sides to facilitate root harvesting, and the seeds were grown for two weeks at 24° C. with 16 h photoperiod.

Expression of the constructs was measured by determining expression levels of the reporter gene for Green Fluorescent Protein (GFP). Preliminary GFP expression (transient) was detected in early transgenic roots during T-DNA transfer. Transgenic roots that developed green callus, growing on shoot-inducing medium containing 50 µg/ml Kanamycin and 100 µg/ml Timentin, were further tested for GFP expression. After several weeks of stringent selection on Kanamycin medium, several independent transgenic Arabidopsis lines were engineered and tested for GFP expression.

Expression was seen both with the Super Ubiquitin promoter including intron and the Super Ubiquitin promoter without the intron. However, preliminary results indicated that the levels of expression obtained with the Super Ubiquitin intron-less promoter construct were significantly higher than those seen with the promoter including intron, suggesting that the intron may contain a repressor. The sequence of the intron is provided in SEQ ID NO: 21.

EXAMPLE 2

Isolation of a CDC Promoter from *Pinus radiata*

Plant EST sequences homologous to the Cell Division Control (CDC) protein gene were isolated from a *Pinus radiata* cDNA expression library as described in Example 1. Using the "Genome Walker" protocol described above and gene specific primers designed from these plant EST sequences, 5'UTR sequence containing the putative promoter of the *P. radiata* CDC gene was isolated from genomic DNA. The determined nucleotide sequence is given in SEQ ID NO.4.

EXAMPLE 3

Isolation of a Xylogenesis-Specific Promoter from *Pinus radiata*

Plant EST sequences specific for plant xylogenesis were isolated from *Pinus radiata* cDNA expression libraries prepared from xylem, essentially as described in Example 1. Using the "Genome Walker" protocol described above and gene specific primers designed from these plant EST sequences, 5' UTR sequence containing a putative *Pinus radiata* xylogenesis-specific promoter was isolated from genomic DNA. The determined nucleotide sequence is provided in SEQ ID NO.5.

EXAMPLE 4

Isolation of a 4-Coumarate-CoA Ligase Promoter from *Pinus radiata*

Plant EST sequences homologous to the 4-Coumarate-CoA Ligase (4CL) gene were isolated from a *Pinus radiata* cDNA expression library as described in Example 1. Using the "Genome Walker" protocol described above and gene specific primers designed from these plant EST sequences, 5'UTR sequence containing the putative promoter of the P. radiata 4CL gene was isolated from genomic DNA. The determined nucleotide sequence is given in SEQ ID NO.6.

DNA constructs comprising the reporter gene for Green Fluorescent Protein (GFP) or GUS reporter genes operably linked to the promoter of SEQ ID NO: 6 were prepared and used to transform *Arabidopsis thaliana* plants.

EXAMPLE 5

Isolation of a Cellulose Synthase Promoter from *Eucalyptus grandis*

Plant EST sequences homologous to the cellulose synthase gene were isolated from a *Eucalyptus grandis* cDNA expression library essentially as described in Example 1. Using the "Genome Walker" protocol described above and gene specific primers designed from these plant EST sequences, 5'UTR sequences containing the putative promoter of the *E. grandis* cellulose synthase gene were isolated from genomic DNA. Independent PCR experiments using different DNA bands as templates yielded two sequences which contained a number of base differences. One band was 750 bp in length and the nucleotide sequence of this band is given in SEQ ID NO:7. The other band was 3 kb in length. The sequence of the 3' end of this band corresponded to the sequence given in SEQ ID NO:7, with a number of base pair differences. The sequence of this 3' end is given in SEQ ID NO:8. The sequence of the 5' end of this band is given in SEQ ID NO:20.

EXAMPLE 6

Isolation of a Leaf-Specific Promoter from *Eucalyptus grandis*

Plant EST sequences specific for leaf were isolated from *Eucalyptus grandis* cDNA expression libraries prepared from leaf tissue, essentially as described in Example 1. Using the "Genome Walker" protocol described above and gene specific primers designed from these plant EST sequences, 5'UTR sequence containing a leaf-specific promoter of a novel *E. grandis* gene (of unknown function) was isolated from genomic DNA. Independent PCR experiments using different DNA bands as templates yielded three sequences which contained a number of base differences and deletions. The determined nucleotide sequences of the three PCR fragments are given in SEQ ID NO: 9–11.

EXAMPLE 7

Isolation of an O-Methyl Transferase Promoter from *Eucalyptus grandis*

Plant EST sequences homologous to an O-methyl transferase (OMT) gene were isolated from a *Eucalyptus grandis* cDNA expression library essentially as described in Example 1. Using the "Genome Walker" protocol described above and gene specific primers designed from these plant EST sequences, 5'UTR sequences containing the putative promoter of the *E. grandis* OMT gene was isolated from genomic DNA. The determined nucleotide sequence is given in SEQ ID NO.12.

DNA constructs comprising the reporter gene for Green Fluorescent Protein (GFP) operably linked to the promoter of SEQ ID NO: 12 were prepared and used to transform *Arabidopsis thaliana*.

EXAMPLE 8

Isolation of a Root-Specific Promoter from *Pinus radiata*

Plant EST sequences homologous to the root-specific receptor-like kinase gene were isolated from a *Pinus radiata* cDNA expression library as described in Example 1. Using the "Genome Walker" protocol described above and gene specific primers designed from these plant EST sequences, 5'UTR sequence containing a putative *P. radiata* root-specific promoter was isolated from genomic DNA. Two independent PCR experiments yielded sequences that contained a number of base differences. The determined nucleotide sequences from the two experiments are given in SEQ ID NO: 13 and 14.

What is claimed is:

1. An isolated polynucleotide comprising SEQ ID NO: 2.

2. An isolated polynucleotide comprising SEQ ID NO: 2 or a fragment thereof having promoter activity.

3. A DNA construct comprising the polynucleotide of claim 1 or 2.

4. A transgenic plant cell comprising the DNA construct of claim 3.

5. A method for producing a plant having modified DNA expression comprising:
   (a) transforming a plant cell with the DNA construct according to claim 3 to provide a transgenic plant cell; and
   (b) cultivating the transgenic plant cell under conditions conductive to regeneration and mature plant growth to produce a modified plant having modified DNA expression compared to an unmodified plant.

6. A method for modifying a phenotype of a plant, comprising stably incorporating into the genome of the plant the DNA construct according to claim 3, and expressing said DNA construct, wherein the expression of said DNA construct modifies the phenotype of the plant.

7. A transgenic plant comprising the transgenic plant cell according to claim 4.

8. A transgenic plant, a fruit or seeds thereof, each comprising the transgenic plant cell according to claim 4.

9. The transgenic plant according to claim 7, wherein said plant is selected from the group consisting of monocotyledonous angiosperms, dicotyledonous angiosperms, and gymnosperms.

10. The transgenic plant according to claim 7, wherein said plant is a woody plant.

11. The transgenic plant of claim 10, wherein said plant is selected from the group consisting of Pinus and Eucalyptus species.

12. A DNA construct comprising, in the 5'-3' direction:
   (a) a promoter sequence,
   (b) a DNA sequence of interest; and
   (c) a DNA termination sequence,
   wherein the promoter sequence comprises the isolated polynucleotide according to claim 2.

13. The DNA construct of claim 12, wherein the DNA sequence of interest comprises an open reading frame encoding a polypeptide of interest.

14. The DNA construct of claim 12, wherein the DNA sequence of interest further comprises an untranslated region of a DNA encoding a polypeptide of interest.

15. The DNA construct of claim 12, wherein the DNA sequence of interest comprises an open reading frame oriented in a sense orientation.

16. The DNA construct of claim 12, wherein the DNA sequence of interest comprises a polynucleotide oriented in an antisense orientation.

17. The DNA construct of claim 12, additionally comprising a nucleotide sequence encoding a selectable marker.

* * * * *

SEQUENCE LISTING

```
<160> NUMBER OF SEQ ID NOS: 21

<210> SEQ ID NO 1
<211> LENGTH: 3083
<212> TYPE: DNA
<213> ORGANISM: Pinus radiata
<220> FEATURE:
<221> NAME/KEY: 5'UTR
<222> LOCATION: (1)...(2064)
<221> NAME/KEY: intron
<222> LOCATION: (1196)...(2033)
<221> NAME/KEY: CDS
<222> LOCATION: (2065)...(2751)
<221> NAME/KEY: 3'UTR
<222> LOCATION: (2755)...(3083)

<400> SEQUENCE: 1
aaaacccctc acaaatacat aaaaaaaatt ctttatttaa ttatcaaact ctccactacc      60
tttcccacca accgttacaa tcctgaatgt tggaaaaaac taactacatt gatataaaaa     120
aactacatta cttcctaaat catatcaaaa ttgtataaat atatccactc aaaggagtct     180
agaagatcca cttggacaaa ttgcccatag ttggaaagat gttcaccaag tcaacaagat     240
ttatcaatgg aaaaatccat ctaccaaact tactttcaag aaaatccaag gattatagag     300
taaaaaatct atgtattatt aagtcaaaaa gaaaaccaaa gtgaacaaat attgatgtac     360
aagtttgaga ggataagaca ttggaatcgt ctaaccagga ggcggaggaa ttccctagac     420
agttaaaagt ggccggaatc ccggtaaaaa agattaaaat tttttttgtag agggagtgct     480 tgaatcatgt tttttatgat ggaaatagat tcagcaccat caaaaacatt caggacacct     540
aaaattttga agtttaacaa aaataacttg gatctacaaa aatccgtatc ggattttctc     600
taaatataac tagaattttc ataactttca aagcaactcc tcccctaacc gtaaaacttt     660
tcctacttca ccgttaatta cattccttaa gagtagataa agaaataaag taaataaaag     720
tattcacaaa ccaacaattt atttcttttta tttacttaaa aaaacaaaaa gtttatttat     780
tttacttaaa tggcataatg acatatcgga gatccctcga acgagaatct tttatctccc     840
tggttttgta ttaaaaagta atttattgtg gggtccacgc ggagttggaa tcctacagac     900
```

-continued

```
gcgctttaca tacgtctcga aagcgtgac ggatgtgcga ccggatgacc ctgtataacc    960
caccgacaca gccagcgcac agtatacacg tgtcatttct ctattggaaa atgtcgttgt   1020
tatccccgct ggtacgcaac caccgatggt gacaggtcgt ctgttgtcgt gtcgcgtagc   1080
gggagaaggg tctcatccaa cgctattaaa tactcgcctt caccgcgtta cttctcatct   1140
tttctcttgc gttgtataat cagtgcgata ttctcagaga gcttttcatt caaaggtatg   1200
gagttttgaa gggctttact cttaacattt gttttctttt gtaaattgtt aatggtggtt   1260
tctgtggggg aagaatcttt tgccaggtcc ttttgggttt cgcatgttta tttggggttat  1320 ttttctcgac tatggctgac attactaggg ctttcgtgct ttcatctgtg ttttcttccc   1380
ttaataggtc tgtctctctg aatatttaa ttttcgtatg taagttatga gtagtcgctg    1440
tttgtaatag gctcttgtct gtaaaggttt cagcaggtgt ttgcgtttta ttgcgtcatg   1500
tgtttcagaa ggcctttgca gattattgcg ttgtactttta atattttgtc tccaaccttg   1560
ttatagtttc cctcctttga tctcacagga acctttctt ctttgagcat tttcttgtgg    1620
cgttctgtag taatatttta atttttgggcc cgggttctga gggtaggtga ttattccagt  1680
gatgtgcttt ccctataagg tcctctatgt gtaagctgtt agggtttgtg cgttactatt   1740
gacatgtcac atgtcacata ttttcttcct cttatccttc gaactgatgg ttcttttttct  1800 aattcgtgga ttgctggtgc catatttat ttctattgca actgtatttt agggtgtctc    1860 tttcttttttg atttcttgtt aatatttgtg ttcaggttgt aactatgggt tgctagggtg   1920
tctgccctct tcttttgtgc ttctttcgca gaatctgtcc gttggtctgt atttgggtga   1980
tgaattattt attccttgaa gtatctgtct aattagcttg tgatgatgtg caggtatatt   2040
cgttagtcat atttcaattt caag atg cag atc ttt gtc aag act ctc acc      2091
                              Met Gln Ile Phe Val Lys Thr Leu Thr
                               1               5 ggt aag acc atc act ctc gag gtc gag agc tct gac acc att gac aat     2139
Gly Lys Thr Ile Thr Leu Glu Val Glu Ser Ser Asp Thr Ile Asp Asn
 10              15                  20                  25 gtt aaa gct aag atc cag gac aag gaa ggg att ccc ccc gac cag cag     2187
Val Lys Ala Lys Ile Gln Asp Lys Glu Gly Ile Pro Pro Asp Gln Gln
         30                  35                  40 cgt ctg atc ttc gca gga aag cag ctt gag gac ggc cga acc ctt gcc     2235
Arg Leu Ile Phe Ala Gly Lys Gln Leu Glu Asp Gly Arg Thr Leu Ala
             45                  50                  55 gat tac aac atc cag aaa gaa tct acc ctc cac ctt gtt ctc cgt ttg     2283
Asp Tyr Asn Ile Gln Lys Glu Ser Thr Leu His Leu Val Leu Arg Leu
 60                  65                  70 agg ggt ggc atg caa atc ttt gta aaa aca cta act gga aag aca att     2331
Arg Gly Gly Met Gln Ile Phe Val Lys Thr Leu Thr Gly Lys Thr Ile
 75                  80                  85 aca ttg gaa gtt gag agc tcg gac acc att gac aac gtc aag gcc aag    2379
Thr Leu Glu Val Glu Ser Ser Asp Thr Ile Asp Asn Val Lys Ala Lys
     90                  95                  100                 105 atc cag gac aag gaa gga att ccc cct gac cag cag agg ctt atc ttc     2427
Ile Gln Asp Lys Glu Gly Ile Pro Pro Asp Gln Gln Arg Leu Ile Phe
                 110                 115                 120 gct ggt aag cag ctg gag gat ggc agg acc ttg gct gat tac aat att     2475
Ala Gly Lys Gln Leu Glu Asp Gly Arg Thr Leu Ala Asp Tyr Asn Ile
             125                 130                 135 caa aag gaa tcg acc ctg cat ttg gtg ctt cgt cta aga gga ggc atg     2523
Gln Lys Glu Ser Thr Leu His Leu Val Leu Arg Leu Arg Gly Gly Met
 140                 145                 150
```

```
caa atc ttt gtg aaa acc ctt aca ggt aaa acc att act ctg gaa gtg    2571
Gln Ile Phe Val Lys Thr Leu Thr Gly Lys Thr Ile Thr Leu Glu Val
    155                 160                 165 gaa agc tcg gac acc att gac aat gtg aag gct aag atc cag gac aag    2619
Glu Ser Ser Asp Thr Ile Asp Asn Val Lys Ala Lys Ile Gln Asp Lys
170                 175                 180                 185 gag gga att cca cct gac cag cag agg ttg atc ttt gcc ggt aag cag    2667
Glu Gly Ile Pro Pro Asp Gln Gln Arg Leu Ile Phe Ala Gly Lys Gln
                190                 195                 200 ctg gaa gat ggt cgt act ctc gcc gat tac aat att cag aag gaa tcg    2715
Leu Glu Asp Gly Arg Thr Leu Ala Asp Tyr Asn Ile Gln Lys Glu Ser
            205                 210                 215 acc ctt cac ctg gtg ctc cgt ctc cgc ggt ggc ttt taggtttggg         2761
Thr Leu His Leu Val Leu Arg Leu Arg Gly Gly Phe
        220                 225 tgttatttgt ggataataaa ttcgggtgat gttcagtgtt tgtcgtattt ctcacgaata  2821
aattgtgttt atgtatgtgt tagtgttgtt tgtctgtttc agaccctctt atgttatatt  2881
tttcttttcg tcggtcagtt gaagccaata ctggtgtcct ggccggcact gcaataccat  2941
ttcgtttaat ataaagactc tgttatccgt tatgtaattc catgttatgt ggtgaaatgt  3001
ggatgaaatt cttagaaatt attattgtaa tttgaaactt ccttcgtcaa taatctgcac  3061
aacacattta ccaaaaaaaa aa                                           3083

<210> SEQ ID NO 2
<211> LENGTH: 2064
<212> TYPE: DNA
<213> ORGANISM: Pinus radiata
<220> FEATURE:
<221> NAME/KEY: 5'UTR
<222> LOCATION: (1)...(2064)
<221> NAME/KEY: intron
<222> LOCATION: (1196)...(2033)

<400> SEQUENCE: 2
aaaccccctc acaaatacat aaaaaaaatt ctttatttaa ttatcaaact ctccactacc    60
tttcccacca accgttacaa tcctgaatgt tggaaaaaac taactacatt gatataaaaa   120
aactacatta cttcctaaat catatcaaaa ttgtataaat atatccactc aaaggagtct   180
agaagatcca cttggacaaa ttgcccatag ttggaaagat gttcaccaag tcaacaagat   240
ttatcaatgg aaaaatccat ctaccaaact tactttcaag aaaatccaag gattatagag   300
taaaaaatct atgtattatt aagtcaaaaa gaaaaccaaa gtgaacaaat attgatgtac   360
aagtttgaga ggataagaca ttggaatcgt ctaaccagga ggcggaggaa ttccctagac   420
agttaaaagt ggccggaatc ccgtaaaaa agattaaaat ttttttgtag agggagtgct   480
tgaatcatgt tttttatgat ggaaatagat tcagcaccat caaaaacatt caggacacct   540
aaaattttga agtttaacaa aaataacttg gatctacaaa aatccgtatc ggattttctc   600
taaatataac tagaatttc ataactttca aagcaactcc tcccctaacc gtaaaacttt   660
tcctacttca ccgttaatta cattccttaa gagtagataa agaaataaag taaataaaag   720
tattcacaaa ccaacaattt atttctttta tttacttaaa aaaacaaaaa gtttatttat   780
tttacttaaa tggcataatg acatatcgga gatccctcga acgagaatct tttatctccc   840
tggttttgta ttaaaaagta atttattgtg gggtccacgc ggagttggaa tcctacagac   900
gcgctttaca tacgtctcga gaagcgtgac ggatgtgcga ccggatgacc ctgtataacc   960
caccgacaca gccagcgcac agtatacacg tgtcatttct ctattggaaa atgtcgttgt  1020
```

-continued

```
tatccccgct ggtacgcaac caccgatggt gacaggtcgc tgttgtcgt gtcgcgtagc      1080 gggagaaggg tctcatccaa cgctattaaa tactcgcctt caccgcgtta cttctcatct      1140
tttctcttgc gttgtataat cagtgcgata ttctcagaga ctttttcatt caaaggtatg      1200
gagttttgaa gggctttact cttaacattt gttttctttt gtaaattgtt aatggtggtt      1260
tctgtggggg aagaatcttt tgccaggtcc ttttgggttt cgcatgttta tttgggttat      1320
ttttctcgac tatggctgac attactaggg ctttcgtgct ttcatctgtg ttttcttccc      1380
ttaataggtc tgtctctctg gaatatttaa ttttcgtatg taagttatga gtagtcgctg      1440
tttgtaatag gctcttgtct gtaaaggttt cagcaggtgt ttgcgtttta ttgcgtcatg      1500
tgtttcagaa ggccttttgca gattattgcg ttgtacttta atattttgtc tccaaccttg      1560
ttatagtttc cctcctttga tctcacagga acccttttctt ctttgagcat tttcttgtgg      1620
cgttctgtag taatattta attttgggcc cgggttctga gggtaggtga ttattccagt       1680
gatgtgcttt ccctataagg tcctctatgt gtaagctgtt agggtttgtg cgttactatt      1740
gacatgtcac atgtcacata ttttcttcct cttatcccttc gaactgatgg ttcttttttct     1800 aattcgtgga ttgctggtgc catatttat ttctattgca actgtatttt agggtgtctc       1860
tttctttttg atttcttgtt aatatttgtg ttcaggttgt aactatgggt tgctagggtg      1920
tctgccctct tcttttgtgc ttctttcgca gaatctgtcc gttggtctgt atttgggtga      1980
tgaattattt attccttgaa gtatctgtct aattagcttg tgatgatgtg caggtatatt      2040
cgttagtcat atttcaattt caag                                              2064
```

<210> SEQ ID NO 3
<211> LENGTH: 1226
<212> TYPE: DNA
<213> ORGANISM: Pinus radiata
<220> FEATURE:
<221> NAME/KEY: 5'UTR
<222> LOCATION: (1)...(1266)

<400> SEQUENCE: 3

```
aaaccccctc acaaatacat aaaaaaaatt ctttatttaa ttatcaaact ctccactacc        60
tttcccacca accgttacaa tcctgaatgt tggaaaaaac taactacatt gatataaaaa       120
aactacatta cttcctaaat catatcaaaa ttgtataaat atatccactc aaaggagtct      180
agaagatcca cttggacaaa ttgcccatag ttggaaagat gttcaccaag tcaacaagat      240
ttatcaatgg aaaaatccat ctaccaaact tactttcaag aaaatccaag gattatagag      300
taaaaaatct atgtattatt aagtcaaaaa gaaaaccaaa gtgaacaaat attgatgtac      360
aagtttgaga ggataagaca ttggaatcgt ctaaccagga ggcggaggaa ttccctagac      420
agttaaaagt ggccggaatc ccggtaaaaa agattaaaat ttttttgtag agggagtgct      480
tgaatcatgt ttttatgat ggaaatagat tcagcaccat caaaaacatt caggacacct      540
aaaattttga agtttaacaa aaataacttg gatctacaaa aatccgtatc ggattttctc      600
taaatataac tagaattttc ataactttca agcaactcc tccctaacc gtaaaactt        660 tcctacttca ccgttaatta cattccttaa gagtagataa agaaataaag taaataaaag     720
tattcacaaa ccaacaattt atttctttta tttacttaaa aaaacaaaaa gtttatttat       780
tttacttaaa tggcataatg acatatcgga gatccctcga acgagaatct tttatctccc      840
tggttttgta ttaaaaagta atttattgtg gggtccacgc ggagttggaa tcctacagac     900
gcgctttaca tacgtctcga gaagcgtgac ggatgtgcga ccggatgacc ctgtataacc     960
```

```
caccgacaca gccagcgcac agtatacacg tgtcatttct ctattggaaa atgtcgttgt    1020
tatccccgct ggtacgcaac caccgatggt gacaggtcgt ctgttgtcgt gtcgcgtagc    1080
gggagaaggg tctcatccaa cgctattaaa tactcgcctt caccgcgtta cttctcatct    1140
tttctcttgc gttgtataat cagtgcgata ttctcagaga cttttcatt caaaggtata     1200 ttcgttagtc atatttcaat ttcaag                                          1226

<210> SEQ ID NO 4
<211> LENGTH: 485
<212> TYPE: DNA
<213> ORGANISM: Pinus radiata
<220> FEATURE:
<221> NAME/KEY: 5'UTR
<222> LOCATION: (1)...(431)
<221> NAME/KEY: TATA_signal
<222> LOCATION: (350)...(356)
<221> NAME/KEY: CAAT_signal
<222> LOCATION: (326)...(333)

<400> SEQUENCE: 4
agtaaaattg gcccatgtag gactaagtca aaatcaaaat tccatctcta aaagcggaac    60
tttgtcccct gaaaattttg actaatttcc aaccaaaaaa agtgggggga aaatataaaa    120
ctctaactaa taaaacaata atcaccaaaa atctatcacc aaaaatgaaa aaagattttg    180
aatactaggc catatgagct acacaaattt caaaagtatc ttacacttat tacgcacccg    240
gatgtcccca ctttcgaaaa acccgtttca agcctttcac gaaagtccaa cggtcagaaa    300
attcaaaatg actgtttgag gcagagccaa tctaggacca cgctccattt atatatggcc    360
tctgcttctc tcgaccctta gagtcctctg ctctgcgaat cttgttgtta gttactgtgt    420
acgctgtaac aatggatgcc tatgagaagt tggagaaggt gggagaagga acctatggga    480
aggtg                                                                485

<210> SEQ ID NO 5
<211> LENGTH: 246
<212> TYPE: DNA
<213> ORGANISM: Pinus radiata
<220> FEATURE:
<221> NAME/KEY: 5'UTR
<222> LOCATION: (1)...(167)
<221> NAME/KEY: TATA_signal
<222> LOCATION: (185)...(191)

<400> SEQUENCE: 5
tgagaacatg ataagctgtg taaattcatg ctagtcacca taacttttct cattgctttt    60
catccacact gttgattcat tcattatata agatcagatt cgtatgatat acaggcaacc    120
atagaaacaa ccagcaaagt tactagcagg aaatccaact aggtatcatg aagactacca    180
acgcaggctc gataatgttg gtgctcatta tttttgggtg ctgtttcatt ggggtcatag    240
ctacat                                                                246

<210> SEQ ID NO 6
<211> LENGTH: 600
<212> TYPE: DNA
<213> ORGANISM: Pinus radiata
<220> FEATURE:
<221> NAME/KEY: 5'UTR
<222> LOCATION: (1)...(167)
<221> NAME/KEY: TATA_signal
<222> LOCATION: (471)...(477)
<221> NAME/KEY: CAAT_signal
<222> LOCATION: (444)...(451)
```

```
<400> SEQUENCE: 6
caccaattta atgggatttc agatttgtat cccatgctat tggctaagcc attttctta      60
ttgtaatcta accaattcca atttccaccc tggtgtgaac tgactgacaa atgcggcccg    120
aaaacagcga atgaaatgtc tgggtgatcg gtcaaacaag cggtgggcga gagaacgcgg    180
gtgttggcct agccgggatg ggggtaggta acggcgtat taccggcgag ttgtccgaat    240
ggagttttcg gggtaggtag taacgtagac gtcaatggaa aaagtcataa tctccgtcaa    300
aaatccaacc gctccttcac accgcagagt tggtggccac gggaccctcc acccactcac    360
tcaatcgatc gcctgccgtg gttgcccatt attcaaccat acgccacttg actcttcacc    420
aacaattcca ggccggcttt cgagacaatg tactgcacag gaaaatccaa tataaaggc    480
cggcctccgc ttccttctca gtagcccca gctcattcaa ttcttcccac tgcaggctac    540
atttgtcaga cacgttttcc gccattttc gcctgtttct gcggagaatt tgatcaggtt    600
```

<210> SEQ ID NO 7
<211> LENGTH: 591
<212> TYPE: DNA
<213> ORGANISM: Eucalyptus grandis
<220> FEATURE:
<221> NAME/KEY: 5'UTR
<222> LOCATION: (1)...(591)
<221> NAME/KEY: TATA_signal
<222> LOCATION: (432)...(437)

```
<400> SEQUENCE: 7
agtttggaat gtgttgtgtg tgatgtgatg gagagtatca gcattccaaa catgacatgg     60
ttttaactta tctgcaatgg tttctttttt attcagcgaa ctcgatggct gatgctgaga    120
gaaatgaatt gggaagtcga tcgacaatgg cagctcaact caatgatcct caggtataag    180
cattttttg gcagctctgg tcattgtgtc ttcaactttt agatgagagc aaatcaaatt    240
gactctaata ccggttatgt gatgagtgaa tcatttgctt ttagtagctt taatttatgc    300
ccccatctta gttgggtata aaggttcaga gtgcgaagat tacatctatt ttggttcttg    360
caggacacag ggattcatgc tagacacatc agcagtgttt ctacgttgga tagtggtatg    420
tacttagcta ctataaagga aattttgata gatatgtttg atatggtgct tgtacagatc    480
tatttaatgt caatgtattt gaaactatct tgtctcataa ctttcttgaa gaatacaatg    540
atgagactgg gaaccctatc tggaagaata gagtggagag ctggaaggac a             591
```

<210> SEQ ID NO 8
<211> LENGTH: 480
<212> TYPE: DNA
<213> ORGANISM: Eucalyptus grandis
<220> FEATURE:
<221> NAME/KEY: 5'UTR
<222> LOCATION: (1)...(480)

```
<400> SEQUENCE: 8
atgctgagag aaatgaattg ggaagtcgat cgacaatggc agctcaactc aatgatcctc     60
aggtataagc atttttttgg cagctctggt cattgtgtct tcaactttta gatgagagca    120
aatcaaattg actctaatac cagttatgtg atgagtgaat catttgcttt tagtagcttt    180
aatttatgcc cccatcttag ttgggtataa aggttcagag tgcgaagatt acatctattt    240
tggttcttgc aggacacagg gattcatgct agacacatca gcagtgtttc tacgttggat    300
agtggtatgt acttagctac tataaaggaa attttgatag atatgtttga tatggtgctt    360
gtacagatct atttaatgcc aatgtatttg aaactatctt gtctcataac tttcttgaag    420
```

<210> SEQ ID NO 9
<211> LENGTH: 308
<212> TYPE: DNA
<213> ORGANISM: Eucalyptus grandis
<220> FEATURE:
<221> NAME/KEY: 5'UTR
<222> LOCATION: (1)...(259)

<400> SEQUENCE: 9

```
gcccatctca ggtgcaacgg tttaactgat gtttactaca cgcaaggggg aggtatccgg      60
aaagcttgca aatcgggtaa aaacgaaaat gggcgacgtg gactcagcct gcccatgttt     120
tcggtctctc tcctggactt ccatgcccga taagggccgc caactctctc tctctctctc     180
tttttctctc acatctctct gcctgttcat gtcgcctgca agtgaagatt cgtcggagca     240
agaaggacga accgggcaca tggcggggtc ggcggtcgcg acggttctaa agggtctctt     300
cctggtgt                                                              308
```

<210> SEQ ID NO 10
<211> LENGTH: 300
<212> TYPE: DNA
<213> ORGANISM: Eucalyptus grandis
<220> FEATURE:
<221> NAME/KEY: 5'UTR
<222> LOCATION: (1)...(251)

<400> SEQUENCE: 10

```
gcccatctca ggtgcaacgg tttaactgat gtttactaca cgcaaggggg aggtatccgg      60
aaagcttgca aatcgggtaa aaacgaaaat gggcgacgtg gactcagcct gcccatgttt     120
tcggtccctc tcctggactt ccatgcccga taaaggccgc caactctctc tcttttctc     180
tcacatctct ctgcctgttc atgtcgcctg caagtgaaga ttcgtcggag caagaaggac     240
gaactgggca tatggcgggg tcggcggtcg cgacggttct aaagggtctc ttcctggtgt     300
```

<210> SEQ ID NO 11
<211> LENGTH: 297
<212> TYPE: DNA
<213> ORGANISM: Eucalyptus grandis
<220> FEATURE:
<221> NAME/KEY: 5'UTR
<222> LOCATION: (0)...(0)

<400> SEQUENCE: 11

```
gtgcaacggt ttaactgatg tttactacac gcaaggggga ggtatccgga aagcttgcaa      60
atcgggtaaa aacgaaaatg ggcgacgtgg actcagcctg cccatgtttt cggtctctct     120
cctggacttc catgcccgat aagggccgcc aactctctct ctctctctct tttctctca     180
catctctctg cctgttcatg tcgcctgcaa gtgaagattc gtcggagcaa gaaggacgaa     240
ctgggcatat ggcggggtcg gcggtcgcga cggttctaaa gggtctcttc ctggtgt       297
```

<210> SEQ ID NO 12
<211> LENGTH: 661
<212> TYPE: DNA
<213> ORGANISM: Eucalyptus grandis
<220> FEATURE:
<221> NAME/KEY: 5'UTR
<222> LOCATION: (1)...(654)
<221> NAME/KEY: TATA_signal
<222> LOCATION: (537)...(543)
<221> NAME/KEY: CAAT_signal

<222> LOCATION: (499)...(502)

<400> SEQUENCE: 12

| | | | | | |
|---|---|---|---|---|---|
| ctgagccatt | taattcgaga | gcacatcgcc | caaaattatt | cttcttgctg | ccataactgt | 60
| cgaattttct | cttttaggta | agtaaccaat | gatgcatcat | gttgacaaaa | aggctgatta | 120
| gtatgatctt | ggagttgttg | gtgcaaattt | gcaagctgac | gatggcccct | cagggaaatt | 180
| aaggcgccaa | cccagattgc | aaagagcaca | agagcacga | tccaaccttt | ccttaacaag | 240
| atcatcacca | gatcggccag | taagggtaat | attaatttaa | caaatagctc | ttgtaccggg | 300
| aactccgtat | ttctctcact | tccataaacc | cctgattaat | ttggtgggaa | agcgacagcc | 360
| aacccacaaa | aggtcagatg | tcatcccacg | agagagagag | agagagagag | agagagagag | 420
| agagttttct | ctctatattc | tggttcaccg | gttggagtca | atggcatgcg | tgacgaatgt | 480
| acatattggt | gtagggtcca | atattttgcg | ggagggttgg | tgaaccgcaa | agttcctata | 540
| tatcgaacct | ccaccaccat | acctcacttc | aatccccacc | atttatccgt | tttatttcct | 600
| ctgctttcct | ttgctcgagt | ctcgcggaag | agagagaaga | gaggagagga | gagaatgggt | 660
| t | | | | | | 661

<210> SEQ ID NO 13
<211> LENGTH: 336
<212> TYPE: DNA
<213> ORGANISM: Pinus radiata

<400> SEQUENCE: 13

| | | | | | |
|---|---|---|---|---|---|
| actagtgatt | tgttgagaat | gagtaggcat | tgctacaccc | atcatcacaa | gcatcatcat | 60
| gaggagaaga | agatccattt | ctcactctat | tactcgaact | tccttcagat | taggctgtgt | 120
| atttctcact | ctaccactcc | aacttccttc | aaatgctgtg | agttttttgtt | gtaattgccc | 180
| cgtctattta | taatcgcagc | agcactcgtc | atataaagac | ccgtgtgtgt | gaacaacaac | 240
| caagtgattt | gaattggaaa | tgaagagcga | gaatggcggt | gtcatgaccg | ggagcaacca | 300
| gcccgggccg | tcgaccacgc | gtgccctata | gtaatc | | | 336

<210> SEQ ID NO 14
<211> LENGTH: 763
<212> TYPE: DNA
<213> ORGANISM: Pinus radiata

<400> SEQUENCE: 14

| | | | | | |
|---|---|---|---|---|---|
| actagtgatt | tgttgagaat | gagtaggcat | tgctacaccc | atcatcacaa | gcatcaacat | 60
| gaagagaaga | agacgatcca | tttctcactc | tatcactcca | acttccttca | gattaggctg | 120
| tgtatttctc | actctaccac | tccaactacc | actccaactt | attgccgcaa | aagagagagg | 180
| ttcccaaact | ctgtcggaat | tctcccactc | aaagcattaa | aggaaagatc | taattgctgc | 240
| aaaaaagaga | gattcccaat | atatttctca | actcccttca | aatgatttct | cactctacca | 300
| ctccaactcc | cttcaaatga | tttctcactc | taccactcca | acttccttca | aatgctgtga | 360
| gttttttgttg | taattgcccc | gtctatttat | aatcgcagca | gcactcgtca | tataaagacc | 420
| cgtgcgtgtg | aacaacaatg | gcggtgtctt | gactgggagc | aaccgcataa | agaaagtggg | 480
| cttcatacat | taaaaaaatc | tgtaaatttt | acggatttgg | aaaaggaag | agcaggaggg | 540
| acctcccgac | ttgacccgag | aatggcggtt | tcttgaccgc | gtaaagaaag | tggtcttctg | 600
| tacccgactt | gacccgaaaa | aagaggaaac | gttgaacgag | acaatctctg | ggaacttcat | 660
| cgaaatgaac | ctcacgactt | gactctttcg | attgtactgt | tttcattgtt | cccgcgtaaa | 720

```
acgaccagcc cgggccgtcg accacgcgtg ccctatagta atc          763
```

<210> SEQ ID NO 15
<211> LENGTH: 40
<212> TYPE: DNA
<213> ORGANISM: Artificial sequence
<220> FEATURE:
<223> OTHER INFORMATION: Made in a lab

<400> SEQUENCE: 15

```
acggataaca gagtctttat attaaacgaa atggtattgc              40
```

<210> SEQ ID NO 16
<211> LENGTH: 51
<212> TYPE: DNA
<213> ORGANISM: Artificial sequence
<220> FEATURE:
<223> OTHER INFORMATION: Made in a lab

<400> SEQUENCE: 16

```
tgacgcggcc gcgaccgacg aaagaaaaa tataacataa gagagtctga a  51
```

<210> SEQ ID NO 17
<211> LENGTH: 27
<212> TYPE: DNA
<213> ORGANISM: Artificial Sequence
<220> FEATURE:
<223> OTHER INFORMATION: Made in a lab

<400> SEQUENCE: 17

```
tatagcggcc gcggggggggg ggggggg                           27
```

<210> SEQ ID NO 18
<211> LENGTH: 30
<212> TYPE: DNA
<213> ORGANISM: Artificial Sequence
<220> FEATURE:
<223> OTHER INFORMATION: Made in a lab

<400> SEQUENCE: 18

```
cggagaacaa ggtggagggt agattctttc                         30
```

<210> SEQ ID NO 19
<211> LENGTH: 31
<212> TYPE: DNA
<213> ORGANISM: Artificial Sequence
<220> FEATURE:
<223> OTHER INFORMATION: Made in a lab

<400> SEQUENCE: 19

```
tctgcatctt gaaattgaaa tatgactaac g                       31
```

<210> SEQ ID NO 20
<211> LENGTH: 363
<212> TYPE: DNA
<213> ORGANISM: Eucalyptus grandis
<220> FEATURE:
<221> NAME/KEY: 5'UTR
<222> LOCATION: (1)...(363)

<400> SEQUENCE: 20
```
aatcgggtga aaatagggcc gccctaaatt agaattgaca catttcttg ggcaaagtta   60 atgtaagtta catgaaaaaa aaaaaaaagg atagtttgtt ggaagtaatg gagcatttgt  120
attgtgaaat tcacgataga gctaacaaaa ataaaggtag ttggtgggtt aacccagtta  180
```

-continued

```
aaaaagaaca ataatttgaa gagaggagag agagagagag gagggggaga gcatttcgat        240
aaattcacta gaaaaaatgc gtgttttagt ataaatgaga gtggaaatag ggccatctag        300
ggaacgatcg atcgcccctg cacccggcca tctggagagt ctgtttatac ttctctccgg        360
ctt                                                                     363

<210> SEQ ID NO 21
<211> LENGTH: 839
<212> TYPE: DNA
<213> ORGANISM: Pinus radiata

<400> SEQUENCE: 21
gtatggagtt ttgaagggct ttactcttaa catttgtttt tctttgtaaa ttgttaatgg         60
tggtttctgt gggggaagaa tcttttgcca ggtccttttg ggtttcgcat gtttatttgg        120 gttattttc tcgactatgg ctgacattac tagggctttc gtgctttcat ctgtgttttc        180
ttcccttaat aggtctgtct ctctggaata tttaattttc gtatgtaagt tatgagtagt        240
cgctgtttgt aataggctct tgtctgtaaa ggtttcagca ggtgtttgcg ttttattgcg        300
tcatgtgttt cagaaggcct ttgcagatta ttgcgttgta ctttaatatt ttgtctccaa        360
ccttgttata gtttccctcc tttgatctca caggaaccct ttcttctttg agcattttct        420
tgtggcgttc tgtagtaata ttttaatttt gggcccgggt tctgagggta ggtgattatt        480
cncagtgatg tgctttccct ataaggtcct ctatgtgtaa gctgttaggg tttgtgcgtt        540
actattgaca tgtcacatgt cacatatttt cttcctctta tccttcgaac tgatggttct        600
ttttctaatt cgtggattgc tggtgccata ttttatttct attgcaactg tattttaggg        660
tgtctctttc tttttgattt cttgttaata tttgtgttca ggttgtaact atgggttgct        720
agggtgtctg ccctcttctt ttgtgcttct ttcgcagaat ctgtccgttg gtctgtattt        780
gggtgatgaa ttatttattc cttgaagtat ctgtctaatt agcttgtgat gatgtgcag        839
```